United States Patent [19]

Shalaby

[11] Patent Number: 5,612,052
[45] Date of Patent: Mar. 18, 1997

[54] HYDROGEL-FORMING, SELF-SOLVATING ABSORBABLE POLYESTER COPOLYMERS, AND METHODS FOR USE THEREOF

[75] Inventor: Shalaby W. Shalaby, Anderson, S.C.

[73] Assignee: Poly-Med, Inc., Anderson, S.C.

[21] Appl. No.: 421,222

[22] Filed: Apr. 13, 1995

[51] Int. Cl.$^6$ ........................................... A61F 2/00
[52] U.S. Cl. .................. 424/426; 528/272; 528/275; 528/354; 528/361; 525/439; 525/450; 424/78.03; 424/78.06; 424/425; 424/457; 424/462; 424/486; 514/506
[58] Field of Search .................................. 528/272, 275, 528/354, 361; 525/439, 450; 424/425, 426, 457, 462, 486, 78.03, 78.06; 514/506

[56] References Cited

U.S. PATENT DOCUMENTS

| | | | |
|---|---|---|---|
| 2,991,766 | 11/1976 | Schmitt et al. | 128/335.5 |
| 4,141,973 | 2/1979 | Balazs | 424/180 |
| 4,209,607 | 6/1980 | Shalaby et al. | 528/291 |
| 4,226,243 | 10/1980 | Shalaby et al. | 128/335.5 |
| 4,369,229 | 1/1983 | Shah | 428/421 |
| 4,532,134 | 7/1985 | Malette et al. | 514/55 |
| 4,911,926 | 3/1990 | Henry et al. | 424/426 |
| 4,919,939 | 4/1990 | Baker | 424/493 |
| 4,938,763 | 7/1990 | Dunn et al. | 604/891.1 |
| 4,994,277 | 2/1991 | Higham et al. | 424/443 |
| 5,011,692 | 4/1991 | Fujioka et al. | 424/426 |
| 5,077,049 | 12/1991 | Dunn et al. | 424/426 |
| 5,093,319 | 3/1992 | Higham et al. | 514/55 |
| 5,135,752 | 8/1992 | Snipes | 424/435 |
| 5,171,148 | 12/1992 | Wasserman et al. | 433/215 |
| 5,198,220 | 3/1993 | Damani | 424/426 |
| 5,278,201 | 1/1994 | Dunn et al. | 523/113 |
| 5,366,733 | 11/1994 | Brizzolara et al. | 424/426 |
| 5,366,756 | 11/1994 | Chesterfield et al. | 427/2.26 |
| 5,385,738 | 1/1995 | Yamahira et al. | 424/489 |

*Primary Examiner*—Samuel A. Acquah

[57] ABSTRACT

The present invention provides novel hydrogel-forming, self-solvating, absorbable polyester copolymers capable of selective, segmental association into compliant hydrogels upon contacting an aqueous environment. Methods of using the novel polyester copolymers of the invention in humans are also disclosed for providing a protective barrier to prevent post-surgical adhesion, treatment of defects in conduits such as blood vessels, and controlled release of a biologically active agent for modulating cellular events such as wound healing and tissue regeneration or therapeutic treatment of diseases such as infection of the periodontium, dry socket, bone, skin, vaginal, and nail infections.

19 Claims, No Drawings

HYDROGEL-FORMING, SELF-SOLVATING ABSORBABLE POLYESTER COPOLYMERS, AND METHODS FOR USE THEREOF

FIELD OF INVENTION

This invention relates generally to biomedical and/or pharmaceutical applications of absorbable or biodegradable polymeric hydrogels. More particularly, the present invention relates to hydrogel-forming, self-solvating, absorbable polyester copolymers capable of selective, segmental association into compliant hydrogels upon contacting an aqueous environment. The invention also discloses methods of using the polyester copolymers of the invention in humans for providing a protective barrier to prevent post-surgical adhesion, a carrier of viable cells or living tissue, treatment of defects in conduits such as blood vessels, and controlled release of a biologically active agent for modulating cellular events such as wound healing and tissue regeneration or therapeutic treatment of diseases such as infection of the periodontium, dry socket, bone, skin, vaginal, and nail infections.

BACKGROUND OF THE INVENTION

Hydrogels are materials which absorb solvents (such as water), undergo rapid swelling without discernible dissolution, and maintain three-dimensional networks capable of reversible deformation (Park, et al., *Biodegradable Hydrogels for Drug Delivery*, Technomic Publishing Co., Lancaster, Pa., 1993; W. Shalaby et al., *J. Controlled Rel.*, 19, 131, 1992; and Silberberg, in *Molecular Basis of Polymer Networks* (Baumgartner, A. & Picot, C. E., Eds.), Spring-Verlag, Berlin, 1989, p. 147).

Covalently crosslinked networks of hydrophilic polymers, including water-soluble polymers are traditionally denoted as hydrogels (or aquagels) in their hydrated state. Hydrogels have been prepared to be based on crosslinked polymeric chains of methoxy poly(ethylene glycol) monomethacrylate having variable lengths of the polyoxyethylene side chains, and their interaction as hydrogels, with blood components have been studied (Nagaoka, et al., in *Polymers as Biomaterials* (Shalaby, S. W., et al., Eds.), Plenum Press, 1983, p. 381). A number of aqueous hydrogels (aquagels) have been used in various biomedical applications, such as, for example, soft contact lenses, wound management, and drug delivery. However, methods used in the preparation of these hydrogels, and their conversion to useful articles, are subject to the constraints associated with the nature of their three-dimensional thermosetting structures and, hence, deprive the users from applying the facile processing techniques employed in the production of non-crosslinked thermoplastic materials.

This, and the low mechanical strength of the hydrated networks, led a number of investigators to explore the concept of combining hydrophilic and hydrophobic polymeric components in block (Okano, et al., *J. Biomed. Mat. Research*, 15, 393, 1981), or graft copolymeric structures (Onishi, et al., in *Contemporary Topics in Polymer Science*, (W. J. Bailey & T. Tsuruta, eds.), Plenum Publ. Co., New York, 1984, p. 149), and blends (Shah, *Polymer*, 28, 1212, 1987; and U.S. Pat. No. 4,369,229) to form the "hydrophobic-hydrophilic" domain systems, which are suited for thermoplastic processing (Shah, Chap. 30, in *Water Soluble Polymers* (S. W. Shalaby, et al., Eds.), Vol. 467, ACS-Symp. Ser., Amer. Chem. Soc., Washington, 1991). The "hydrophobic-hydrophilic" domain system (HHDS) undergoes morphological changes which are associated with the hydration of the hydrophilic domains and formation of pseudo-crosslinks via the hydrophobic component of the system (Shah, 1991, cited above). Such morphology was considered to be responsible for the enhanced biocompatibility and superior mechanical strength of the two-phase HHDS as compared to those of covalently crosslinked, hydrophilic polymers. The mechanism of gel formation in the present invention parallels that described by Shah, 1991, cited above, for non-absorbable blends of hydrophilic-hydrophobic domain systems (HHDS). However, differences exist between the copolymers of the present invention, and more particularly, Component "A", and HHDS. In this regard, Component A is based on a water-soluble and water-insoluble block structure (SIBS). This is not a mere physical mixture of two polymers as are the blends described by Shah, 1991, cited above. Additionally, due to the presence of covalent links between the blocks of SIBS, the resulting hydrogel displays higher elasticity compliance and tensile strength while being absorbable. In fact, the SIBS systems are, in some respects, analogous to thermoreversible gels (Shalaby, in *Water-Soluble Polymers*, (Shalaby, S. W., et al., Eds.), Vol. 467, Chapt. 33, ACS Symp. Ser., Amer. Chem. Soc., Washington, D.C., 1991a) in displaying a hydration-dehydration equilibrium governing the system transformation, i.e., the gel/liquid equilibrium is driven by the water content of the SIBS. Thus, in the absence of water, the polyoxyalkylene blocks undergo intermolecular segmental mixing with the neighboring hydrophobic blocks to produce a viscous liquid. In the presence of water, competition between the water as an extrinsic solvent and the polyester block for the polyoxyalkylene (POA) block forces the hydration of the POA, and aggregation or association of the polyester blocks to establish pseudo-crosslinks which maintain a 3-dimensional integrity. Since gel formation takes place in an aqueous environment, the POA block will preferentially migrate to the exterior of the gel and interface with the adjoining tissues to establish an adhesive joint, which prevents gel migration from target site and sustains its intended efficacy. As for example, for periodontal and dry socket applications, post-surgical adhesion prevention and treatment of vaginal and bone infections, and other applications where predictable site residence of the gel cannot be compromised.

Synthesis and biomedical and pharmaceutical applications of absorbable or biodegradable hydrogels based on covalently crosslinked networks comprising polypeptide or polyester components as the enzymatically or hydrolytically labile components, respectively, have been described by a number of researchers (Jarreit, et. al., *Trans. Soc. Biomater.*, Vol. XVIII, 182, 1995; Pathak, et. al., *Macromolecules*, 26, 581, 1993; Park, et. at., *Biodegradable Hydrogels for Drug Delivery*, Technomic Publishing Co., Lancaster, Pa., 1993; Park, *Biomaterials*, 9, 435, 1988; and W. Shalaby, et. al., 1992, cited elsewhere herein). The hydrogels most often cited in the literature are those made of water-soluble polymers, such as polyvinyl pyrrolidone, which have been crosslinked with naturally derived biodegradable components such as those based on albumin (Park, et. al., 1993, cited elsewhere herein; and W. Shalaby, et. al., 1992, cited elsewhere herein). Totally synthetic hydrogels which have been studied for controlled drug release and membranes for the treatment of post-surgical adhesion are based on covalent networks formed by the addition polymerization of acrylic-terminated, water-soluble chains of polyether dl-polylactide block copolymers (Jarrett, et. al., 1995, cited elsewhere herein; and Pathak, et al., 1993, cited elsewhere herein).

Polymer solutions which undergo reversible gelation by heating or cooling about certain temperatures (lower critical solution temperature, LCST) are known as thermoreversible gels. Theoretical and practical aspects of key forms of thermoreversible gels are described by Shalaby, 1991a, cited elsewhere herein. Among the thermoreversible gels discussed by Shalaby are those of amorphous N-substituted acrylamides in water and amorphous polystyrene and crystalline poly(4-methyl pentene) in organic solvents. Prevailing gel formation mechanisms include molecular clustering of amorphous polymers and selective crystallization of mixed phases of crystalline materials. Thermodynamic parameters (enthalpy and entropy) which favor gel formation in terms of LCST are discussed by Shalaby only with respect to the solvent-polymer interaction. Shalaby fails, however, to address self-solvating chains.

U.S. Pat. No. 4,911,926, discloses aqueous and non-aqueous compositions comprised of block polyoxyalkylene copolymers that form gels in the biologic environment, for preventing post-surgical adhesion. Other gel forming compositions for use in preventing post-surgical adhesion include: (a) chitin derivatives (U.S. Pat. No. 5,093,319); (b) aqueous solutions of xanthan gum (U.S. Pat. No. 4,994,277); (c) chitosan-coagulum (U.S. Pat. No. 4,532,134); and (d) hyaluronic acid (U.S. Pat. No. 4,141,973).

Absorbable polymers, or often referred to as biodegradable polymers, have been used clinically in sutures and allied surgical augmentation devices to eliminate the need for a second surgical procedure to remove functionally equivalent non-absorbable devices (U.S. Pat. No. 3,991,766, to Schmitt et al.; and Shalaby, in *Encyclopedia of Pharmaceutical Technology* (J. C. Boylan & J. Swarbrick, eds.), Vol. 1, Dekker, New York, 1988, p. 465). Although these devices were designed for repairing soft tissues, interest in using such transient systems, with or without biologically active components, in dental and orthopedic applications has grown significantly over the past few years. Such applications are disclosed in Bhatia, et. al., *J. Biomater. Sci.*, Polym. Ed., 6(5), 435, 1994; U.S. Pat. No. 5,198,220, to Damani; U.S. Pat. No. 5,171,148, to Wasserman, et. al.; and U.S. Pat. No. 3,991,766, to Schmitt et al.

U.S. Pat. No. 3,991,766, to Schmitt et al., discloses absorbable articles made of polyglycolide acid, such as sutures, clips and storage pallets having medicaments incorporated therein and can be used for both their own mechanical properties and delayed release systems of medicaments. U.S. Pat. No. 5,171,148, to Wasserman et al., discloses the use of absorbable polymers made from p-dioxanone or L-lactide and glycolide as dental inserts for the treatment of periodontal disease. Here, a semiporous mesh material with sealed edges is emplaced between the tooth and gingiva. The implant is attached to the tooth by an absorbable ligature material. U.S. Pat. No. 5,198,220, to Damani, discloses the treatment of periodontal disease through the use of a sustained release composition/device comprising bioactive agents. The composition/device is in a liquid, semi-solid or solid form suitable for insertion into or around the periodontal pocket. Damani also teaches the formation of a gel, or paste, composition consisting of poly(lactyl-co-glycolide) in an acceptable solvent (such as propylene carbonate), with or without propylene and/or polyethylene glycol, and an antibiotic agent such as tetracycline hydrochloride.

Other in-situ forming biodegradable implants and methods of forming them are described in U.S. Pat. Nos. 5,278,201 ('201 Patent) and U.S. Pat. No. 5,077,049 ('049 Patent), to Dunn et al. The Dunn et al., patents disclose methods for assisting the restoration of periodontal tissue in a periodontal pocket and for retarding migration of epithelial cells along the root surface of a booth. The '049 Patent discloses methods which involve placement of an in-situ forming biodegradable barrier adjacent to the surface of the tooth. The barrier is microporous and includes pores of defined size and can include biologically active agents. The barrier formation is achieved by placing a liquid solution of a biodegradable polymer, such as poly(dl-lactide-co-glycolide) water-coagulatable, thermoplastic in a water miscible, non-toxic organic solvent such as N-methyl pyrrolidone (i.e., to achieve a typical polymer concentration of $\leq 50\%$) into the periodontal pocket. The organic solvent dissipates into the periodontal fluids and the biodegradable, water coagulatable polymer forms an in-situ solid biodegradable implant. The dissipation of solvent creates pores within the solid biodegradable implant to promote cell ingrowth. The '859 Patent likewise discloses methods for the same indications involving the formation of the biodegradable barrier from a liquid mixture of a biodegradable, curable thermosetting prepolymer, curing agent and water-soluble material such as salt, sugar, and water-soluble polymer. The curable thermosetting prepolymer is described as an acrylic-ester terminated absorbable polymer.

The '049 and '859 Patents, as well as U.S. Pat. No. 4,938,763 to Dunn et al., disclose polymer compositions primarily consisting of absorbable thermoplastic or thermosetting polymer, dissolved in organic solvent. These compositions are also described to produce, in an aqueous environment, solids which can be used as tissue barrier (Fujita, et. al., *Trans. Soc. Biomater.*, Vol. XVII, 384, 1994) substrate for tissue generation (Dunn, et. al., *Poly. Prepr.*, 35(2), 437, 1994a) or carrier for the controlled delivery of drugs (Sherman, et. al., *Pharm. Res.*, 11(105–318, 1994). Acrylate-endcapped poly(caprolactone) prepolymer was also used as a branched precursor for the in-situ formation of a crosslinked system for potential use in controlled drug release (Moore, et. at., *Trans. Soc. Biomater.*, Vol. XVIII, 186, 1995).

A number of controlled delivery systems for the treatment of periodontal disease are also described in the literature. For example, U.S. Pat. No. 4,919,939, to Baker, discloses a controlled release delivery system for placement in the periodontal pocket, gingival sulcus, tooth socket, wound or other cavity within the mouth. The system incorporates microparticles in fluid medium and is effective in the environment of use for up to 30 days. The drug, in 10–50 micron polymer particles, is released at a controlled rate by a combination of diffusion of the drug through the polymer and erosion of the polymer.

U.S. Pat. No. 5,135,752, to Snipes, discloses a buccal dosage form, which melts in the oral cavity, yet will not spontaneously deform at higher temperatures encountered in shipment and storage. This composition comprises two grades of polyethylene glycol, polyethylene oxide, long-chain saturated fatty acid, and colloidal silica.

U.S. Pat. No. 5,366,733, to Brizzolars et al., discloses an oral composition for the local administration of a therapeutic agent to a periodontal pocket comprising at least one therapeutic agent dispersed in a matrix including a biocompatible and/or biodegradable polymer. The composition is administered as a plurality of dry discrete microparticles, said microparticles are prepared by a phase separation process. An oral composition is also described wherein the polymer comprises a block copolymer of polyglycolide, trimethylene carbonate and polyethylene oxide. Apparatus and methods are also provided for dispensing the dry microparticles to the periodontal pocket, whereby they become tacky and adhere to the involved tissue so as to induce long-term therapeutic effects.

In addition, a number of systems for the controlled delivery of biologically active compounds to a variety of sites are disclosed in the literature. For Example, U.S. Patent No. 5,011,692, to Fujioka et al., discloses a sustained pulsewise release pharmaceutical preparation which comprises drug-containing polymeric material layers. The polymeric material layers contain the drug only in a slight amount, or free of the drug. The entire surface extends in a direction perpendicular to the layer plane and is coated with a polymeric material which is insoluble in water. These types of pulsewise-release pharmaceutical dosages are suitable for embedding beneath the skin.

U.S. Pat. No. 5,366,756, to Chesterfield et al., describes a method for preparing porous bioabsorbable surgical implant materials. The method comprises providing a quantity of particles of bioabsorbable implant material, and coating particles of bioabsorbable implant material with at least one growth factor. The implant can also contain antimicrobial agents.

U.S. Pat. No. 5,385,738, to Yamahira et al., discloses a sustained-release injection system, comprising a suspension of a powder comprised of an active ingredient and a pharmaceutically acceptable biodegradable carrier (e.g., proteins, polysaccharides, and synthetic high molecular weight compounds, preferably collagen, atelo collagen, gelatin, and a mixture thereof) in a viscous solvent (e.g., vegetable oils, polyethylene glycol, propylene glycol, silicone oil, and medium-chain fatty acid triglycerides) for injection. The active ingredient in the pharmaceutical formulation is incorporated into the biodegradable carrier in the following state: (i) the active ingredient is chemically bound to the carrier matrix; (ii) the active ingredient is bound to the carrier matrix by intermolecular action; or (iii) the active ingredient is physically embraced within the carrier matrix.

Furthermore, a common complication which is encountered by many surgeons following tooth extraction is dry socket. Dry socket occurs following three to four percent of routine extractions (Field, et. al., *J. Oral Maxillofac. Surg.*, 23(6), 419, 1985), and its etiology appears to be multifactorial (Westerholm, *Gen. Dent.*, July–Aug., 306, 1988). Over the years, dry socket has been referred to as alveoloalgia, alveolitis sicca dolorosa, avascular socket, localized osteitis, fibrinolytic alveolitis and localized acute alveolar osteomyelitis (Shafer, et al., *A Textbook of Oral Pathology*, 4th Ed., W. B. Saunders Co., Philadelphia, 1974, p. 605, 1974; and Birn, *Int. J. Oral Surg.*, 2, 211, 1973). Although many chemotherapeutic prevention measures or management have been pursued, none have significantly reduced the incidence of dry socket (Birn, 1973, cited above; Field, el. al., 1985, cited above). Among such approaches to the therapeutic treatment of dry socket, with limited success, are those based on systemic administration of antibiotics (Westerholm, 1988, cited above) or direct placement of powdered sulfadiazine or sulfathiazole into the socket (Elwell, *J. Amer. Dent. Assoc.*, 31, 615, 1944).

To date, the known HHDS and thermoreversible gels can be classified as non-absorbable materials and are expected not to absorb through chain dissociation in the biological environment. Meanwhile, there is a growing interest in developing absorbable sutures and allied surgical devices such as transient implants, which are degraded to bioabsorbable, safe by-products and leave no residual mass at the surgical site, as well as frequently cited clinical advantages (Shalaby, Chap. 3 in *High Technology Fibers* (M. Lewin & J. Preston, eds.), Dekker, New York, 1985; Shalaby, 1988, cited elsewhere herein; Shalaby, *Polym. News*, 16, 238, 1991; Shalaby, *J. Appl. Biomater.*, 3, 73, 1992; Shalaby, *Biomedical Polymers: Designed to Degrade Systems*, Hanser Publ., New York, 1994; and Shalaby, et al, eds. *Polymers of Biological & Biomedical Significance*, Vol. 520, ACS-Symp. Ser., Amer. Chem. Soc., Washington, 1993) have justified the need for novel absorbable hydrogel formulations.

Moreover, such systems as those previously described in the literature, for example, such as by Dunn, et al, (U.S. Pat. No. 4,938,763), teach in-situ formations of biodegradable, microporous, solid implants in a living body through coagulation of a solution of a polymer in an organic solvent such as N-methyl-2-pyrrolidine. However, the use of solvents, including those of low molecular organic ones, facilitates migration of the solution from the application site thereby causing damage to living tissue including cell dehydration and necrosis. Loss of the solvent mass can lead to shrinkage of the coagulum and separation from surrounding tissue.

Furthermore, currently available drug delivery systems deal with solid implants which can elicit mechanical incompatibility and, hence, patient discomfort. The present invention provides novel, hydrogel-forming copolymers, which in contrast to those systems previously described, are absorbable, do not require the use of solvents, and are compliant, swollen, mechanically compatible gels, which adhere to surrounding tissue.

SUMMARY OF THE INVENTION

The primary object of the present invention is to provide a hydrogel-forming, self-solvating, absorbable polyester copolymer capable of selective, segmental association into a compliant hydrogel mass on contact with an aqueous environment.

Another object of the present invention, is to provide such a copolymer optionally comprising a biologically active agent.

Yet another object of the present invention, is to provide such a copolymer optionally comprising a low molecular weight component.

A further object of the present invention, is to provide such a copolymer capable of the controlled-release of a biologically active agent/drug for modulating cellular events, such as, wound healing and tissue regeneration.

A further object of the present invention, is to provide such a copolymer capable of the controlled-release of a biologically active agent/drug for therapeutic treatment of diseases, such as, infection of the oral cavity, dry socket, bone, skin, vaginal and nail infections.

A further object of the present invention, is to provide such a copolymer which is capable of being extruded or injected into living tissue, or onto the surface thereof, for providing a protective barrier for treating conditions, such as, post-surgical adhesion.

A further object of this invention is to provide such a copolymer for constituting or constructing a carrier of vaccines, living cells, or viable tissue for sustaining biological functions both in vitro and in vivo.

A further object of the present invention, is to provide such a copolymer which is capable of acting as a blocking agent or sealant for treating defects in conduits.

Accordingly, the present invention provides hydrogel-forming, self-solvating, absorbable polyester copolymers capable of selective, segmental association into a compliant hydrogel mass on contact with an aqueous environment. In a preferred embodiment of the invention, the copolymer comprises a base component, designated "Component A" herein. As used herein, the terms "Component A" and "copolymer(s)" are interchangeable and refer to the basic structure of the copolymers of the invention. Component A comprises a molecular chain having a hydrophilic block, designated "Y" herein, and a relatively hydrophobic polyester block, designated "X" herein. Hydrophobic block X and hydrophilic block Y more preferably comprises a molecular structure having the following formula: X-Y-X or $(X-Y)_n$, and branched structures thereof. Most preferably, hydrophobic block X comprises a polyester formed by grafting a glycolide, lactide, ε-caprolactone, p-dioxanone, trimethylene carbonate or combinations thereof, onto the hydroxylic or amino groups of a hydrophilic polymer precursor i.e., Y; hydrophilic block Y comprises a polyoxyethylene, poly(oxyethylene-b-oxypropylene), polypeptide polyalkylene oxamate, a polysaccharide, and derivatives thereof; or a liquid, high molecular weight polyether glycol interlinked with an oxalate or succinate functionalities in linear or branched form.

Component A optionally comprises carboxylic endgroups formed by any known technique in the art, such as, for example, end-group succinylation. This facilitates ionically binding a biologically active agent or drug to Component A, such that, drug release can be modulated. The biologically active agent or drug is preferably present on Component A in an insoluble form, such as, (1) a microparticulate dispersion, (2) a surface-deposited coating onto an absorbable microporous microparticles, and/or (3) ionically bound molecules onto the surfaces of absorbable microporous microparticles.

In another embodiment of the invention, Component A optionally comprises an absorbable carrier associated therewith and, designated "Component B" herein. As used herein, the term "associated therewith" refers to any chemical and/or physical means known in the art for combining components together. The function of Component B is to carry the biologically active agent. This is preferably desirable for medications which call for an initial drug burst and prolonged release thereafter and, thus, highly regulated availability of drugs at the biological site.

In a further embodiment of the invention, Component A, with or without component B and/or the biologically active agent, optionally comprises a similarly constituted low molecular weight block copolyester associated therewith. The low molecular weight copolyester preferably is a plasticizer and, more preferably, the plasticizer is designated "Component C" herein.

It is understood that Component A, with or without the biologically active agent/drug and/or compositions of Components A, B, C, the biologically active agent, and variations thereof, can provide a wide range of properties for treating a host of diseases, including, but not limited to, dental, orthopedic and vascular applications. For example, the copolymers of the invention can: (1) be extruded or injected into living tissue or onto the surface of living tissues to provide a protective barrier to prevent post-surgical adhesion; (2) act as a blocking agent or sealant for treatment of defect in conduits such as blood vessels; (3) facilitate the controlled-release of a biologically active agent/drug for modulating cellular events such as wound healing and tissue regeneration or therapeutic treatment of diseases such as infection of the periodontium, dry socket, bone, skin, vaginal, and nail infections; and (4) facilitate the sustained in vitro or in vivo growth of viable cells and/or living tissues for the purpose of tissue engineering.

DETAILED DESCRIPTION OF THE INVENTION

The term "Hydrophobic Block(s)" as used herein, refers to absorbable polyester chain block(s) or segment(s) of variable length which, is present in an isolated form, will produce practically amorphous (with less than 5% crystallinity) or totally amorphous material having a $T_g$ of less than 25° C., and preferably, is a viscous liquid at room temperature. Hydrophobic block(s) X comprises copolymeric segments of known chemistries in the art, such as, those comprised from cyclic lactones (e.g., glycolide, l-lactide, dl-lactide, ε-caprolactone, p-dioxanone, trimethylene carbonate), polyalkylene oxalate, and the like, as described by Shalaby, 1988, cited elsewhere herein, which disclosure is hereby incorporated by reference. More preferably, hydrophobic segment(s) or block(s) X comprises lactide/glycolide copolymer (with 51 to 80% l- or dl-lactide).

The term "Hydrophilic Block(s)" as used herein, refers to polymeric blocks or segments which, if present in an isolated form, will be water soluble. Hydrophilic block(s) or segment(s) Y comprises poly(oxyethylene), with or without a minor component of a higher homolog, such as, poly(oxypropylene)-polypeptide, polyalkylene oxamate (Shalaby et al., 1980, cited elsewhere herein, which disclosure is hereby incorporated by reference), a polysaccharide, or derivatives thereof. The length of the hydrophilic block and its weight fractions can be varied to modulate the rate of gel formation, its modulus, its water content, diffusivity of bioactive drug through it, its adhesiveness to surrounding tissue, and bioabsorbability.

The term "Hydrogel" or "Hydrogel Mass" as used herein, refers to materials which have a high tendency for water absorption and/or retention, and maintain mechanical integrity through physical crosslinks which are reversible in nature.

The term "Physical Crosslinks" as used herein, refers to a three-dimensional structure which is held together by physical quasi or pseudo crosslinks, or ionic bonds, as compared to covalently crosslinked. These physical crosslinks facilitate the reversibility of the hydrogel. This reversibility property can be influenced by external factors, such as, solvent or heat.

The term "Self-Solvating" as used herein, refers to components of chains which in the absence of external factors i.e., solvents, have greater affinity for physical interaction such that the components are capable of forming a virtually one phase system.

The term "Compliant" as used herein, refers to a material having a low modulus and which is easily deformable.

The term "Biologically Active Agent" as used herein broadly includes any composition or compound of matter which when dispensed in the chosen environment of use produces a predetermined, beneficial and useful result.

The term "Drug" or "Agent" as used herein broadly includes physiologically or pharmacologically active substances for producing a localized effect at the administration site or a systemic effect at a site remote from the administration site.

The term "Plasticizer" as used herein, refers to an absorbable polyester composition with hydrophilic and hydrophobic components similar, or identical to, those of Component A, with the exception of having a higher hydrophilic/hydrophobic ratio in Component C than Component A.

The present invention discloses novel hydrogel-forming, self-solvating, absorbable polyester copolymers, which upon hydration results in a hydrogel mass. The hydrogel mass is stabilized by pseudo-crosslinks provided by a hydrophobic polyester component, such as those comprised from cyclic lactones e.g., glycolide, l-lactide, dl-lactide, ε-caprolactone, p dioxanone, trimethylene carbonate, polyalkylene oxalate, derivatives thereof and the like, covalently linked to a hydrophilic component comprised of blocks, such as those derived from a polyethylene glycol, polypeptide, polyalkylene oxamate (U.S. Pat. Nos. 4,209,607 and 4,226,243, to Shalaby et al., hereby incorporated by reference), or polysaccharide and derivatives thereof. The polyester copolymers, with or without modifying additives, undergo hydration in the biologic environment leading to selective segmental association thereby forming compliant hydrogels at the application site.

These copolymers are especially useful for localized, controlled delivery of biologically active agents/drugs and protecting or augmenting damaged, compromised, and/or traumatized tissues. More particularly applications of the novel copolymers of the invention include: (a) the treatment of periodontal disease, wherein a tetracycline- or chlorhexidine-containing hydrogel-former is injected in the periodontal pocket to form an adhesive gel or semi-solid mass in the pocket for the controlled release of such antimicrobial drugs over a period of 2 to 45 days. Near the practical exhaustion of the drug, the polymer will commence to absorb substantially as it undergoes advanced stages of degradation; (b) the prevention and treatment of dry socket with formulations similar to those of Component A; (c) providing a hydrogel barrier with or without non-steroidal anti-inflammatory drugs on traumatized tissue to prevent post-surgical adhesion; (d) applications as an antimicrobial hydrogel for the treatment of vaginal infections; (e) treatment of bone diseases such as osteomyelitis, with injectable formulations comprising antibiotics including gentamicin and vancomycin; (f) accelerating tissue regenerating in compromised soft and hard tissue, e.g., fractured bone, ulcers, burns, by employing formulations comprising growth promoters, such as growth factors or their oligomeric analogs; and, (g) treatment of diseases such as psoriasis and infected nails using formulations comprising antimicrobial agents. Other applications of the hydrogel-forming copolymers of the invention include (a) blood vessel sealant; (b) vascular blocking agent; (c) carrier for injectable anti-inflammatory formulations in the treatment of joint diseases; and (d) active carrier of viable cells or living tissue.

The copolymers of the invention comprise a primary or base component designated "Component A" herein. Component A comprises molecular chains having a hydrophilic block, designated "Y" herein, and a relatively hydrophobic polyester block, designated "X" herein. The molecular structure of hydrophobic block X and hydrophilic block Y preferably comprises one of the following formulas: X-Y-X or $(X-Y)_n$, and branched structures thereof. More preferably, hydrophobic block X comprises a polyester formed by grafting a glycolide, lactide, ε-caprolactone, p-dioxanone, trimethylene carbonate or combinations thereof, onto the hydroxylic or amino-end groups of a hydrophilic polymer precursor i.e., Y. Hydrophilic block Y preferably comprises a polyoxyethylene, poly(oxyethylene-b-oxypropylene), polypeptide, polyalkylene oxamate, a polysaccharide, or derivatives thereof, or a liquid, high molecular weight polyether glycol interlinked with oxalate or succinate functionalities in linear or branched form.

In a preferred embodiment, Component A comprises a polyethylene glycol having a molecular weight of about 400 Daltons which is pre-interlinked with succinate or oxalate bridges to increase the length of the hydrophilic block and, thus, the molecular weight of A without favoring its crystallization. That is, the hydrophilic prepolymer "Y" having hydroxylic end-groups, is end-grafted with a mixture 60/40 dl-lactide/glycolide to produce a block copolymer having a hydrophilic block fraction "Y" of about 0.25. To render Component A more receptive to basic drugs, its end-groups can optionally be carboxylated, for instance, by their acylation with succinic anhydride. Component A, with or without a biologically active agent, is introduced to a biological target site using conventional means and, thereafter, undergoes selective-segmental segregation to form a flexible, compliant, reversible gel which adheres to the surrounding tissues and acquires the configuration of the site. Component A of the invention more preferably comprises an inherent viscosity at 25° C. in chloroform ranging between 0.03 to 0.80 dL/g and can be present as a liquid at room temperature, or practically amorphous material (with less than 5% crystallinity) with a $T_g$ of less than 25° C., which can be extruded through a die or administered through a syringe needle.

Component A comprises copolymeric chains with self-solvating components (analogous to phase mixing of two component miscible blends) to allow its existence as a viscous, extrudable material at room temperature, and its transformation to a flexible reversible hydrogel upon administration to a biological site. These hydrogels adhere tenaciously to adjacent tissues and acquire the shape of the site. The present copolymers are mechanically compatible in highly sensitive sites, as well as, can mediate external mechanical stresses or shocks. As such, the copolymers of the invention can be applied easily without incorporating a major extrinsic water-soluble, potentially cytotoxic organic solvent in order to facilitate upon administration in-situ coagulation to a solid mass.

Component A, with or without a non-steroidal anti-inflammatory drug (NSAID) or active polypeptide, can be used as a protective barrier, a blocking agent of vascular defects caused by needle puncturing, a sealant of damaged surfaces for preventing post-surgical adhesion or as a carrier of immunostimulants or viable cells. Component A, mixed with an antimicrobial agent/drug, can be injected or applied topically with a suitable known applicator for the treatment of bone, cartilage, nail, skin, and vaginal infections.

In another embodiment of the invention, Component A optionally includes a biologically active agent/drug, such as, an antimicrobial agent, anesthetic agent, antibiotic, and/or a peptide or protein, for regulating cellular events. The biologically active agent/drug can comprise by way of illustration, antifungal agents, antibacterial agents, antibiotics, anti-inflammatory agents, immunosuppressive agents, immunostimulatory agents, dental densitizers, odor masking agents, immune reagents, anesthetics, antiseptics, nutritional agents, antioxidants, lipopolysaccharide complexing agents, peroxides, tissue growth factors, a mixture of any of the foregoing, and the like. The agent/drug can be deposited, wholly or in part, on Component A, with or without carboxy-terminated ends. In an alternative embodiment, the biologically active agent/drug can be deposited, wholly or in part, on a solid carrier, designated "Component B" herein. Component B preferably is an absorbable, powder prior to mixing with Component A and, more preferably, Component B is an absorbable, microporous low molecular weight polyester which is highly crystalline and practically insoluble in Component A.

A preferred formulation of Components A/B comprises a mixture of 20/80 B/A, with B being a low molecular, microporous polyglycolide with 0.70 to 0.95 solid fraction, average particle size of 0.5–200 micron and carboxyl-bearing chains. High concentration of carboxylic groups on the chains can be achieved by preparing Component B using di- or poly-carboxylic acid as initiators. The deposited agent on Component B can exhibit a release profile which can be multiphasic, including: (a) simple, fast diffusion of soluble free drug through gel A; (b) slow diffusion of soluble free drug housed in the pores of B; and, (c) drug release at the surface (both exterior and pore) of B or the chain ends of carboxylated A chains by ion exchange of ionically bound molecules. By varying the concentration of Component B in Component A, the flow characteristics and release profile of the agent can be modulated. This is important because in certain applications, the flow characteristic or properties of Component A/B formulations can determine the clinical efficacy, particularly in cases of treating periodontal disease, nail infection and bone infection where high viscoelasticity (due to the high weight fraction of the microparticulate dispersed phase and its physicomechanical interlocking with viscous liquid continuous phase A) of the gel composite is pertinent to assure mechanical stability at the target site.

Component A optionally includes an absorbable low molecular weight component. This component can modulate the rheological properties, gel-formation time, and mechanical disposition of Component A at the target site. The low molecular-weight component preferably is a plasticizer and, more preferably, the plasticizer is designated "Component C" herein. Component C can (a) aid the dispersion of Component B in Component A; (b) reduce the overall system viscosity of Component A/B formulation, (c) reducing the viscosity and facilitating the injectability of Component B if used alone or with a biologically active compound, and/or (d) increase the rate of hydration or gel formation. The absorbable plasticizer, such as Component C, is capable of modulating the viscosity and/or gel-formation rate of Component A, with or without Component B, thereby broadening its applicability. Highly viscous forms of Component A can be easily plasticized with a low molecular weight (inherent viscosity of 0.03–0.15) polyester copolymer Component C, that is made of the same chemical entities as Component A, (but different hydrophilic weight fraction) to produce easily injectable liquid systems.

In a more preferred embodiment, Component A is formed by end-grafting a polyethylene glycol having a molecular weight of about 400–900 Dalton with a mixture of glycolide and l- or dl-lactide in the presence of stannous octoate as a catalyst to produce a block copolymer with (a) ether/ester mass ratios of 20–49/80–51, preferably 25–40/75–55 and, most preferably 30–40/70–60; (b) having an inherent viscosity in chloroform at 25° C. from about 0.03 to 0.80, preferably from about 0.1 to 0.6, more preferably from about 0.15 to 0.5, and most preferably from about 0.2 to 0.4 dL/g; and (c) is in the form of an extrudable, essentially amorphous, semi-solid having a $T_g$ of less than 25° C., preferably an amorphous material having a $T_g$ of less than 37° C., and more preferably a viscous liquid at room temperature that can be easily administered through a syringe needle.

In a still more preferred embodiment, copolymer Component A is formed by end-grafting an oxalate- or succinate-interlinked liquid polyethylene glycol having a molecular weight of more than 1200 Dalton with a mixture of glycolide and l- or dl-lactide in the presence of stannous octoate as a catalyst to produce a block copolymer with (a) ether/ester mass ratio of 20–49/80–51 and preferably 25–40/75–55 but most preferably 30–40/70–60; (b) having an inherent viscosity in chloroform at 25° C. of about 0.03 to 0.80, preferably 0.1 to 0.60, more preferably, 0.15 to 0.50, and most preferably, 0.2 to 0.4 dL/g; and (c) in the form of extrudable, essentially amorphous semi-solid having a $T_g$ of less than 25° C. and preferably an amorphous material having a $T_g$ of less than 25° C. and, more preferably, a viscous liquid at room temperature that can be easily administered through a syringe needle.

Formulations comprised of the polyester copolymers of the invention are suitable carriers of biologically active agents/drugs at typical loading levels of 0.02 to 20%. The chain of Component A or Component C can be succinylated to provide acidic end-groups for ionic binding of the agents/drugs. Liquid compositions made of Component A or Components A/C, with or without agnet/drug, can form hydrogels upon contacting a liquid environment. This is achieved through the hydration of the hydrophilic block of the copolymeric chains leading to intramolecular conformational changes and association of the hydrophobic blocks as pseudo-crosslinks in a reversible, hydrophilic/hydrophobic hydrogel system.

For copolymer formulations comprising the agent, such morphology provides a suitable environment for the controlled release of the agent. The agent can be present in a soluble or dispersed form. Preferably, the agent is deposited on a micronized powder, more preferably a microporous absorbable powder and, most preferably, a powder (Component B) which offers an ion-binding, high surface area for ionically immobilizing part of the soluble agent to control its release and, thus, produce copolymers with a multiphasic release profile over a period of 2 to 45 days.

More specifically, the biologically active agents can be present as (a) a solute in Component A; (b) a dispersed solid in Component A; (c) a coating on Component B; (d) ionically bound molecules on Components A and/or B; and/or (e) mechanically held within the pores of Component B. Each of these forms of drug will have its own release pathway and, thus, bio-availability at the site. Depending on the concentration of Component B, the hydrogel-forming formulation can be made to have a broad range of properties and gel-formation kinetics to allow its use in many applications.

Component A with a biologically active agent and/or Components B and/or C, is used for treatment of periodontal disease, osteomyalitis, and dry socket. While a discussion follows for using the copolymers of the invention for treatment of periodontal disease, it is understood that this discussion is for purposes of illustration only and, not limitation, and the copolymers of the invention have broad applications of use. Periodontal disease, as used herein, is a general term for a number of diseases that affect the periodontal tissue. These diseases are characterized by a range of symptoms including inflammation, bleeding, exudation of pus from the gingival sulcus, deepening of the sulcus to form periodontal pockets, tissue lesions, loss of connective tissue, alveolar bone loss, and ultimately tooth loosening and loss. The primary cause of periodontal disease is now believed to be bacterial infection of the plaque that forms on tooth surfaces below the gingival margin. The copolymer formulations of the present invention are useful for prolonged, controlled dispensing of a range of drugs and agents, such as, for example: (a) prophylactic prolonged application of minerals and ions, such as calcium or fluoride ion; (b) prolonged controlled exposure to local antiseptics, including, chlorhexidine and tibezonium iodide; (c) controlled antibiotic delivery, including such antibiotics as aminoglycosides, macrolides such as erythromycin, penicillins, cephalosporins and the like; (d) anesthetic/analgesic delivery pre- or post surgery or to treat other mouth pain using such agents as amide-type local anesthetics like lidocaine, mepivacaine, pyrrocaine, bupivacaine, prilocaine, etidocaine, or the like; and (e) local controlled delivery of non-steriodal anti-inflammatory drugs such as ketorolac, naproxen, diclofenac sodium and fluribiprofen. It is recognized that in certain forms of therapy, combinations of agents/drugs in the same delivery system i.e., copolymer of the invention, can be useful in order to obtain an optimal effect. Thus, for example, an antibacterial and an anti-inflammatory agent may be combined in a single copolymer to provide combined effectiveness.

It has also been recently shown that regrowth and repair of periodontal connective tissue can be encouraged with the aid of polypeptide mitogenic growth factors. See, for example, V. P. Terranova et al., Biochemically Medicated Periodontal Regeneration, J. Periodont. Res., 22, pages 248–251, incorporated herein by reference. The copolymers of the present invention can be designed to release appropriate encapsulated, or uncapsulated, growth factors, including, epidermal growth factors, human platelet derived TGF-B, endothelial cell growth factors, thymocyte-activating factors, platelet derived growth factors, fibroblast growth factor, fibronectin or laminin.

The drug/agent can be used at a level of from about 0.1% to a about 70%, preferably form about 1% to about 50%, most preferably form about 2% to about 30%. The copolymers of the invention can be designed to release drug to provide a steady state number average concentrations of from about 1 µg to about 2000 µg, preferably form about 20 µg to about 1200 µg, most preferably from about 50 µg to about 800 µg per milliliter of the gingival crevicular fluid of a treated periodontal pocket. The steady state release rates can be altered by varying component ratios of the copolymer formulations. The steady state conditions are preferably used since initial bursts are accounted for as well as delays in release. For example, in the case of a ten (10) day therapy, steady state is generally reached in about one to two days. More preferably, a formulation for treating periodontal disease comprises 20/80 Components B/A, containing 1–3% of an active drug such as chlorhexidine or tetracycline.

In addition to the agent/drug, the copolymer formulations of the present invention can include a variety of optional components. Such components include, but are not limited to, surfactants, viscosity controlling agents, medicinal agents, cell growth modulators, dyes, complexing agents, antioxidants, other polymers such as carboxymethly cellulose, gums such as guar gum, waxes/oils such as castor oil, glycerol, dibutyl phthalate and di(2-ethylhexyl) phthalate as well as man others. If used, such optional components comprise form about 0.1% to about 20%, preferably from about 0.5% to about 5% of the total copolymer formulation.

The copolymers of the invention can be inserted into the periodontal pocket or gingival region, and can be administered in the form of a particle, film or sheet. The size, shape and thickness can be changed according to the condition of the disease to be treated. Ordinarily, the size, shape and thickness are changed according to the size of the periodontal pocket of the patient or the condition of the gingiva.

In another embodiment of the invention, there is contemplated pharmaceutical formulations comprising the copolymers of the invention. For example, a preferred pharmaceutical formulation comprises an injectable viscous fluid of Component A, Components A/B, Components A/B/C and/or Components A/C, containing about 0.01% to 10% agent/drug and, more preferably about 0.2% to 5% of agent/drug. The released of the agent/drug is over a period of 1 to 45 days and, more preferably 2 to 30 days. The drug/agent can include anti-microbials, such as, chlorhexidine, tetracycline, and metronidazole; antibiotics, such as, gentamicin and vancomycin; and compounds which can accelerate wound healing or tissue regeneration, prevent post-surgical adhesion, neoplastic formation, and prevent or accelerate blood clotting.

In another embodiment of the pharmaceutical formulation, the copolymer comprises part or all of the bioactive agent deposited on a microporous and/or finely divided absorbable powder, such as, those consisting of low molecular weight crystalline polyglycolide or copolyglycolide. The powder is formed by low to moderate conversion (that is 60–95% ) ring-opening polymerization of glycolide or a mixture made predominantly of glycolide and small amounts of other lactones. The polymerization is carried out in the presence of stannous octoate as a catalyst and sufficient concentration of glycolic acid as an initiator to produce a mass. Upon quenching, grinding, roll-milling in an inert medium, and extraction with water, 2-propanol, microporous particles are produced having (a) 1 to 200µ diameter and, more preferably 10–150 g; (b) an inherent viscosity in hexafluoro-2-propanol at 25° C. of <0.03 to 0.3 and, more preferably <0.05 to 0.2 dL/g; (c) contain less than 2% residual monomer; and (d) have 0.03 to 0.35 and, more preferably 0.05 to 0.25 pore fraction.

An important difference between conventional formulations in the art and the novel copolymers of the invention, is that the present copolymers do not include the use of organic solvents. Such solvents can compromise the copolymers shelf-stability, as in the case of a polyester in a basic solvent such as N-methyl-pyrrolidine, which can catalyze chain dissociation in the presence of trace amounts of moisture. The prior art formulations also teach the use of other reactive solvents such as propylene glycol (which degrades the polyester chain through alcoholysis), or trimethylene carbonate (which can copolymerize with the polyester chain). Moreover, should the prior art formulations be radiation sterilized, the presence of a solvent can lead to the generation of new chemical species originating from the solvent as well as in combination with the bioactive ingredient. In effect, organic solvents described in the prior art can compromise the purity and efficacy of both the drug (optional) and polymer which can, in turn, be associated with unsafe use.

Another feature of the novel copolymers of the invention, is that when administered to a biological site the copolymers do not experience discernible reduction in organic mass, as is the case of prior art compositions which coagulate in-situ by leaching out a major water-soluble component. Leaching out a major water-soluble components can be associated with shrinkage and separation from the surrounding tissue and, in some instances, uncontrolled formation of microporous mass. Because the copolymers of the invention are comprised of copolymeric chains, the copolymers can be easily tailored to modulate its viscosity without the intervention of a new chemical species, such as, an organic solvent.

A further feature of the novel copolymers of the invention, is that since the copolymers are comprised of self-solvating molecules, its conversion to a hydrogel about a drug provides a uniform distribution of the therapeutic agent, and thus, more reproducible release profile, in contrast with prior art systems where complex physical events prevail due to the presence of leachable solvents.

The following Examples are provided to further illustrative the present invention, and should not be construed as limitations thereof:

EXAMPLE I

PREPARATION OF COMPONENT "A"

1. Preparation of 79/21 (by weight) Block Copolymer of 60/40 dl-Lactide/Glycolide and Polyethylene Glycol 400

A suitable flask was thoroughly cleaned, flame-dried, and charged dry with polyethylene glycol (MW-400; 5 g, 0.0125 mole), dl-lactide (12 g, 0.083 mole), glycolide (6.4 g, 0.056 mole), stannous octoate catalyst (0.4M in toluene; 34.7 μL, 0.014 mmole), and a magnetic stirrer under nitrogen condition. The reactor was placed in an oil bath and heated to 170° C. under a positive nitrogen pressure for 16 hours. The flask was removed and stored open in a vacuum oven. The inherent viscosity (IV) of the composition was determined using a 50 capillary viscometer (Ostwald type) at a concentration of 0.1 g/100 mL in chloroform. In a constant temperature bath set at 30° C., the IV was determined to be 0.13 dL/g. A DuPont 990 Differential Scanning Calorimeter (DSC) was used to determine glass transition ($T_g$) of the material. Approximately 4 mg of the sample was heated at 10° C./min from −50° C. in a nitrogen environment. $T_g$=−41° C.

2. Preparation of 60/40 (by weight) Block Copolymer of 60/40 dl-Lactide/Glycolide and Polyethylene Glycol 400 Interlinked with Oxalate Functionality Polyethylene glycol (MW=400; 4.1 g, 0.01 mole), dimethyl oxalate (3.1 g, 0.025 mole), and stannous octoate catalyst (0.4M in toluene; 883 μL, 0.035 mmole) were mixed in a dry glass reactor containing a magnetic stirrer and heated to 150° C. under a nitrogen atmosphere for 4 hours. A vacuum of less than 0.1 mm Hg was applied to remove the condensate (methanol) and excess dimethyl oxalate. The reactor was then cooled to approximately 50° C. and PEG (MW=400; 8.3 g, 0.021 mole) was added. The reactants were heated to 150° C. for 3 hours before applying vacuum and cooling to room temperature. dl-Lactide (13.3 g, 0.093 mole), glycolide (7.2 g, 0.062 mole) were added under dry conditions to the reactor. The flask was heated to 150° C. under a positive nitrogen pressure for 12 hours. Next, the temperature was increased to 170° C. for 3.5 hours and vacuum was applied for 2 hours as the flask cooled to room temperature. The polymer was isolated and stored under vacuum.

IV in $CHCl_3$=0.11 dL/g

3. Preparation of 78/22 (by weight) Block Copolymer of 60/40 dl-Lactide/Glycolide and Polyethylene Glycol 400 Interlinked with Oxalate Functionality Polyethylene glycol (MW=400; 2.0 g, 0.005 mole), dimethyl oxalate (1.77 g, 0.015 mole), and stannous octoate catalyst (0.2M in toluene; 90.5 gL, 0.036 mmole) were mixed in a dry glass reactor containing a magnetic stirrer and heated to 140° C. under a nitrogen atmosphere for 2 hours. A vacuum of less than 0.1 mm Hg was applied to remove the condensate (methanol) and excess dimethyl oxalate. The reactor was then cooled to approximately 50° and PEG (MW=400; 4.2 g, 0.011 mole) was added. The reactants were heated to 155° C. for 1 hour under slight vacuum before increasing the temperature to 160° C. for 2 hours under increased vacuum. l-Lactide (14.4 g, 0.1 mole), glycolide (7.7 g, 0.066 mole) were added under dry conditions to the reactor. The flask was heated to 150° C. under a positive nitrogen pressure for 15 hours. Next, the temperature was lowered to 130° C. and vacuum was applied. The material bubbled violently, indicating the presence of monomer. A strong vacuum was applied as the material cooled to room temperature. The final product was washed with 2-propanol at 40° C. for about 20 minutes to remove the excess monomer before drying under vacuum at room temperature.

The weight average molecular weight ($MW_w$) and polydispersity index (PDI) of the material was determined using a Waters Gel Permeation Chromatography (GPC) apparatus. The instrument consisted of a 600E control Module and Solvent Delivery System, a U6K injector, three Syragel HT linear columns in series, a 401 Differential Refractometer detector, and a 746 Data Module. Chloroform was used as the mobile phase at a flow rate of 1 mL/min. and polystyrene molecular weight standards were used to calibrate the system. $MW_w$:5723; PDI:2.42

4. Preparation of 68/32 (by weight) Block Copolymer of 60/40 dl-Lactide/Glycolide and Polyethylene Glycol 400

Polyethylene glycol (MW=400; 15 g, 0.0375 mole), dl-lactide (21 g, 0.146 mole), glycolide (11.3 g, 0.097 mole), and stannous octoate catalyst (0.2M in toluene; 243 μL, 0.049 mmole) were added under dry conditions to a glass reactor containing a magnetic stirrer. The reactor was placed in an oil bath and heated to 150° C. under a positive nitrogen pressure for 1 hour, then to 160° C. for 6 hours. The flask was cooled under a vacuum of less than 0.1 mm Hg and placed in a vacuum oven.

$MW_w$:1670; PDI:1.46

5. Preparation of 68/32 (by weight) Block Copolymer of 60/40 dl-Lactide/Glycolide and Polyethylene Glycol 400 Interlinked with Oxalate Functionality Polyethylene glycol (MW=400; 160 g, 0.4 mole), dimethyl oxalate (47.2 g, 0.4 mole) and stannous octoate catalyst (0.2M in toluene; 200 μL, 0.04 mmole) were mixed under a dry nitrogen environment and heated to 150° C. for 1 hour. The temperature was increased to 160° C. for 2 hours before applying a vacuum of 1 mm Hg and allowing to cool to approximately 50° C. Then, 5 g of PEG 400 were added and the reaction was continued at 160° for 0.5 hours. Finally, 15 g of the interlinked PEG were mixed with dl-lactide (21 g, 0.146 mole), glycolide (11.3 g, 0.097 mole), and stannous octoate catalyst (0.2M in toluene; 243 ηL, 0.049 mmole were added under dry conditions to a glass reactor containing a magnetic stirrer. The reactor was heated to 150° C. under a positive nitrogen pressure for 1 hour, then to 160° C. for 6 hours. The flask was cooled under a vacuum of less than 0.1 mm Hg and stored in a vacuum oven.

$MW_w$:4713; PDI:2.41

6. Preparation of 73/27 (by weight) Block Copolymer of 60/40 dl-Lactide/Glycolide and Polyethylene Glycol 400

Polyethylene glycol (MW 400; 12.5 g), dl-lactide (22.5 g, 0.156 mole), glycolide (12.1 g, 0.104 mole), and stannous octoate catalyst (0.2M in toluene 260 μL, 0.052 mmole) were added to a dry glass reactor containing a magnetic stirrer. The reactor was heated to 150° C. under a positive nitrogen pressure for 18 hours. The flask was cooled under a vacuum of less than 0.1 mm Hg for 0.5 hours and stored in a vacuum oven. $MW_w$:2172; PDI:1.53

7. Preparation of 73/27 (by weight) Block Copolymer of 60/40 dl-Lactide/Glycolide and Polyethylene Glycol 400 Interlinked with Oxalate Functionalities Interlinked PEG (12.5 g, described in Example 5), dl-lactide (22.5 g, 0.156 mole), glycolide (12.1 g, 0.104 mole), and stannous octoate catalyst (0.2M in toluene; 260 μL, 0.052 mmole) were added to a dry glass reactor containing a magnetic stirrer. The reactor was heated to 150° C. under a positive nitrogen pressure for 18 hours. The flask was cooled under a vacuum of less than 0.1 mm Hg for 0.5 hours and stored in a vacuum oven. $MW_w$:5723; PDI:2.41

8. Preparation of 68/32 (by weight) Block Copolymer of 60/40 dl-Lactide/Glycolide and Polyethylene Glycol 400 Interlinked with Oxalate Functionalities Interlinked PEG (15 g, described in Example 5), dl-lactide (21 g, 0.146 mole), glycolide (11.3 g, 0.097 mole), and stannous octoate catalyst (0.2M in toluene; 243 µL, 0.049 mmole) were added to a dry glass reactor containing a magnetic stirrer. The reactor was heated to 150° C. under a positive nitrogen pressure for 3 hours and then 160° C. for 3 hours. The flask was cooled under a vacuum of less than 0.1 mm Hg for 0.5 hours and stored in a vacuum oven. $MW_w$:3582; PCI:2.08

EXAMPLE II

PREPARATION OF COMPONENT "B"

1. Preparation of Polyglycolide (PG) Drug Carrier

Glycolic acid (0.46 g, 0.006 mole), glycolide (34.8 g, 0.30 mole), and stannous octoate catalyst (0.4M in toluene; 150 µL, 0.06 mmole) were mixed in a dry flask equipped with a magnetic stirrer under a dry nitrogen atmosphere. The reactants were slowly heated to 170° C. (approx. 20 min.) under agitation. At this time, the reactants formed an opaque mixture and the temperature was increased again to 200° C. When the temperature reached 176° C., the material was translucent and the viscosity was very high. The flask was then removed from heat and quenched with liquid nitrogen for about 2 minutes. The glassware was broken and removed and the reactants were dropped in the liquid nitrogen to terminate the reaction completely. The resulting PG solid was dried in a vacuum oven at 35° C. overnight. Using a Wiley mill with a 60 mesh sieve, the PG was ground to a fine powder. The entrapped monomer was extracted using anhydrous acetone at 35° C. resulting in porous particles of PG.

2. Addition of Chlorhexidine Diacetate to PG Carrier

Chlorhexidine diacetate (8.7 g) was dissolved in approximately 500 mL of isopropyl alcohol in a roto-evaporator at 38° C. The extracted PG powder (25.6 g) (Example II-1) was added to the solution and the mixture was agitated for 6 hours under a slight vacuum. The temperature was increased to 40° C. and a stronger vacuum was applied to distill 2-propanol and acetic acid. When all of the 2-propanol had displaced, the temperature was decreased to 35° C. and the agitation was continued for another 2 hours. The resulting white powder was scraped from the containing flask and placed in a vacuum oven at 35° C. overnight. The powder was then mixed with mineral oil (1:2) and treated in a 3-roll mill for about 5 min. The oil was removed using heptane and the dry particles were shown to have an average diameter of 16 micron.

3. Preparation of Drug Carrier B-Polyglycolide

Same as in Example II-1, except using the following polymerization charge and scheme:

| Charge: | Glycolide | 34.8 g (0.3 mole) |
|---|---|---|
| | Glycolic acid | 2.28 g (0.03 mole) |
| | Stannous octoate | 0.06 mmole |

Scheme: The polymerization charge was heated to 160° C. and maintained at that temperature with stirring for 15 minutes when the polymer crystallized. The product was cooled, isolated, broken into small pieces, and ground using a Wiley mill.

The ground polymer was mixed with about 2 parts mineral oil and roll-milled to achieve the desired particle size (about 5 min). The particles were isolated from the mineral oil as described in Example 10 and were shown to have an average diameter of 50 micron. The micronized polymer was then extracted with 2-propanol as described in Example II-1. Dry weight data indicated a 7% weight loss. Titration of the accessible carboxylic group of the particle reflects a value of 0.3 mmole/g.

4. Loading Carrier B with Chlorhexidine

One gram of Carrier B from Example II-3 was stirred with deionized water for 20 min., filtered, and air dried. Solid B particles were mixed with 150 mg of chlorhexidine diacetate in 80% aqueous acetone at 25° C. for 1 hour and 40° C. for 1 hour, cooled and then filtered. Analysis of the filtrate (using UV spectrophotometry) indicates that 80% of the drug is retained by the carrier.

EXAMPLE III

PREPARATION OF COMPONENT "C"

1. Preparation of 14/86 (by weight) of Block Copolymer of 60/40 dl-Lactide/Glycolide and Polyethylene Glycol 400

Polyethylene glycol (MW=400; 20 g, 0.05 mole), dl-lactide (2.12 g, 0.015 mole), glycolide (1.14 g, 0.010 mole), and stannous octoate catalyst (0.4M in toluene; 25 µL, 0.05 mmole) were added under dry conditions to a glass rector containing a magnetic stirrer. The reactor was heated to 130° C. to melt the reactants and then increased to 170° C. to start the reaction. After 5 hours, the system was cooled and stored in a vacuum oven. $MW_w$:503; PDI:1.23

2. Preparation of 14/86 (by weight) of Block Copolymer of 60/40 dl-Lactide/Glycolide and Polyethylene Glycol 400 Interlinked with Oxalate Functionalities PEG 400 was interlinked with dimethyl oxalate (as described in Example 5) prior to the addition of dl-lactide and glycolide. Interlinked PEG (85 g), dl-lactide (9.0 g, 0.0625 mole), glycolide (4.83 g, 0.0417 mole), and stannous octoate catalyst (0.2 M in toluene; 105 µL, 0.05 mmole) were added to a dry glass reactor and heated to 150° C. for 1 hours. The temperature was increased to 160° C. for 4 more hours before removing the reactants from heat and applying a vacuum of less than 0.1 mm Hg as the material cooled to room temperature. The polymer was isolated and stored under vacuum.

EXAMPLE IV

PREPARATION OF CHLORHEXIDINE (CHX)

DELIVERY SYSTEM

Example 1: Preparation of Drug Delivery System (1.0:0.09:0.31:0.01, A:B:C:CHX by weight)

Component C (1.20 g-Example III [1]) and Component B (0.40 g—Example II[2]) were added to 4.3 g of Component A (Example I[1]). The materials were mixed at slightly elevated temperatures (approximately 40° C.) to obtain a uniform distribution. Chlorhexidine (0.04* g) was added to the mixture to make a final composition consisting of 70.5% A, 6.5% B, 22% C, and 1% free drug. [* Based on the weight of diacetate salt].

Example 2: Preparation of Drug Delivery System (1.0:0.1;0.25;0.01,A:B:C:CHX by weight)

Component C (1.67 g—Example III[1]) and Component B (0.51 g—Example II[2]) were added to 4.77 g of Component A (Example I[3]) and mixed to obtain a uniform distribution. Chlorhexidine (0.05 g) was mixed into the system to make up the following composition by weight: 68% A, 7% B, 24% C, and 1% free drug.

EXAMPLE V

DRUG RELEASE FORMULATION

Samples of drug carrier (Component B) were loaded with chlorhexidine as described in Example II[4] were mixed with gel-former Component A from Examples I [4] and [5]. Another set of formulations were made of drug-bearing B, gel-former A, and plasticizer C (Example III[1]). All formulations were roll-milled for 1 to 3 minutes, transferred to a syringe, and into a 21 gauge needle. The formulations were then injected into water for subjective comparative assessment of their rate of gel formation texture and mechanical integrity. A rating of 1 to 5 was adapted for this evaluation with 1 being the fastest. A summary of these formulation compositions and ratings is provided in Table 1.

TABLE 1

Composition and Gel-Formation of Drug Delivery Formulations

| D Number | Source of A Ex. 4. % | Source of B Ex. 5. % | Source of C Ex. 12. % | Ex. 13. % | Gel-Formation Rating |
|---|---|---|---|---|---|
| 17-1 | 40 | 40 | 20 | 0 | 4 |
| 17-2 | 30 | 55 | 15 | 0 | 4 |
| 17-3 | 30 | 40 | 30 | 0 | 5 |
| 17-4 | 40 | 30 | 30 | 0 | 3 |
| 17-5 | 45 | 25 | 30 | 0 | 3 |
| 17-6 | 40 | 20 | 40 | 0 | 3 |
| 17-7 | 0 | 50 | 30 | 20 | 1 |
| 17-8 | 30 | 40 | 20 | 10 | 2 |

It is understood that the Examples described herein are for purposes of illustration only and, not limitation, and that various modification and/or changes that may suggest themselves to one skilled in the art are intended to be included within the spirit of this application and the scope of the appended claims.

We claim:

1. A hydrogel-forming, self-solvating absorbable polyester copolymer capable of selective, segmental association into a compliant hydrogel mass on contact with an aqueous environment.

2. The copolymer of claim 1, wherein said copolymer comprises a hydrophobic polyester block X covalently bonded to a hydrophilic block Y.

3. The copolymer of claim 1, wherein said copolymer is carboxy-terminated.

4. A composition comprising:
   the copolymer according to claim 1; and
   a biologically active agent associated with said copolymer.

5. The copolymer of claim 4, wherein said agent is at least partially deposited on an absorbable, microparticulate solid carrier.

6. The copolymer of claim 4, wherein said agent is bonded to said copolymer.

7. The copolymer of claim 5, wherein carrier is a microporous carrier.

8. The copolymer of claim 2, wherein said blocks X and Y are covalently bonded together in an arrangement selected from the group consisting of X-Y-X, $(X-Y)_n$, and branched structures thereof.

9. The copolymer of claim 8, wherein said hydrophilic block Y comprises less than 50 % of the mass of said copolymer.

10. The copolymer of claim 9, wherein said hydrophilic block Y comprises oxyethylene or a combination of oxyethylene and oxypropylene sequences.

11. The copolymer of claim 8, wherein said hydrophobic block X comprises greater than 50% of the mass of said copolymer.

12. The copolymer of claim 11, wherein said hydrophobic block is derived from ring opening polymerization of lactones or step-growth formation of alkylene oxalates.

13. The copolymer of claim 1, wherein said copolymer is extrudable.

14. The copolymer of claim 13, wherein said extrudable copolymer is a liquid.

15. The copolymer of claim 14, wherein said liquid is capable of being injectable into a biological site.

16. The copolymer of claim 14, wherein said liquid is obtained by combining a high molecular weight sample of said copolymer with a lower molecular weight component.

17. The copolymer of claim 16, wherein said lower molecular weight component is a plasticizer.

18. The copolymer of claim 17, wherein said plasticizer comprises said polymer wherein the hydrophilic block Y to hydrophobic block X ratio is greater than 1.

19. The copolymer of claim 1, wherein said hydrogel mass is reversible into a liquid.

\* \* \* \* \*